United States Patent
Shimoyama et al.

(10) Patent No.: US 9,546,948 B2
(45) Date of Patent: Jan. 17, 2017

(54) GAS SENSOR

(71) Applicants: The University of Tokyo, Tokyo (JP); OMRON Corporation, Kyoto-shi (JP)

(72) Inventors: Isao Shimoyama, Tokyo (JP); Kiyoshi Matsumoto, Tokyo (JP); Tetsuo Kan, Tokyo (JP); Yusuke Takei, Tokyo (JP); Hidetoshi Takahashi, Tokyo (JP); Koutaro Ishizu, Tokyo (JP); Masahito Honda, Tokyo (JP)

(73) Assignees: The University of Tokyo, Tokyo (JP); Omron Corporation, Kyoto-shi (JP)

( * ) Notice: Subject to any disclaimer, the term of this patent is extended or adjusted under 35 U.S.C. 154(b) by 0 days.

(21) Appl. No.: 14/368,396

(22) PCT Filed: Dec. 27, 2012

(86) PCT No.: PCT/JP2012/083880
§ 371 (c)(1),
(2) Date: Jun. 24, 2014

(87) PCT Pub. No.: WO2013/105450
PCT Pub. Date: Jul. 18, 2013

(65) Prior Publication Data
US 2015/0009503 A1    Jan. 8, 2015

(30) Foreign Application Priority Data
Jan. 13, 2012   (JP) ................. 2012-004964

(51) Int. Cl.
*G01N 21/27* (2006.01)
*G01N 21/552* (2014.01)
*G01N 33/00* (2006.01)

(52) U.S. Cl.
CPC ............ *G01N 21/27* (2013.01); *G01N 21/553* (2013.01); *G01N 33/004* (2013.01);
(Continued)

(58) Field of Classification Search
CPC ...................................... G01N 21/27
See application file for complete search history.

(56) References Cited

U.S. PATENT DOCUMENTS 8,920,729 B2 * 12/2014 Rong ............... G01N 21/55
                                                    385/12
2003/0032039 A1 * 2/2003 Cunningham et al. ........ 435/6
(Continued)

FOREIGN PATENT DOCUMENTS

JP    S62-123348 A    6/1987
JP    H02138857 A    5/1990
(Continued)

OTHER PUBLICATIONS

International Search Report issued in PCT/JP2012/083880, dated Jan. 29, 2013.
(Continued)

*Primary Examiner* — Tarifur Chowdhury
*Assistant Examiner* — Omar Nixon
(74) *Attorney, Agent, or Firm* — Locke Lord LLP

(57) ABSTRACT

A gas sensor is proposed, which can detect a gas by a novel configuration while reduction in size is achieved. The gas sensor (1) does not need a light absorption path as in a prior art so that the size can be reduced correspondingly. Further, in the gas sensor (1), a gas is absorbed in an ionic liquid (IL), and a dielectric constant of the ionic liquid (IL) that changes by absorbing the gas can be measured according to a change in light intensity that occurs by a surface plasmon resonance phenomenon in a metal layer (7). Thus, the gas sensor (1) including the novel configuration that can detect a gas based on the change in the light intensity can be realized.

10 Claims, 23 Drawing Sheets

(52) U.S. Cl.
CPC ... *G01N 33/0036* (2013.01); *G01N 2201/067* (2013.01); *G01N 2201/0612* (2013.01)

(56) References Cited

U.S. PATENT DOCUMENTS

| | | | | |
|---|---|---|---|---|
| 2006/0234391 | A1* | 10/2006 | Weiss | G01N 33/552 436/518 |
| 2007/0132043 | A1 | 6/2007 | Bradley et al. | |
| 2007/0172894 | A1* | 7/2007 | Genick | B01L 3/5085 435/7.2 |
| 2008/0103056 | A1* | 5/2008 | Lin | B01L 3/5085 506/9 |
| 2008/0212102 | A1* | 9/2008 | Nuzzo | G01N 21/554 356/445 |
| 2009/0008629 | A1 | 1/2009 | Matsumoto et al. | |
| 2010/0128273 | A1* | 5/2010 | Lee et al. | 356/445 |
| 2010/0326825 | A1* | 12/2010 | Hane et al. | 204/431 |
| 2011/0205543 | A1* | 8/2011 | Offermans et al. | 356/445 |

FOREIGN PATENT DOCUMENTS

| | | |
|---|---|---|
| JP | H03237350 A | 10/1991 |
| JP | 04000223 B2 | 1/1992 |
| JP | 06079009 B2 | 10/1994 |
| JP | 2004085392 A | 3/2004 |
| JP | 2006222279 A | 8/2006 |
| JP | 2007505323 A | 3/2007 |
| JP | 2010192599 A | 9/2010 |
| JP | 2010197181 A | 9/2010 |
| JP | 2010203838 A | 9/2010 |
| JP | 2010261793 A | 11/2010 |
| WO | WO-2011155179 A1 | 12/2011 |

OTHER PUBLICATIONS

S. Miwa et al., "Selective gas detection by means of surface plasmon responance sensors," Thin Solid Films 281-282, 446-468, (1996).

S. Neethirajan et al., "Carbon Dioxide ($CO_2$) Sensors for the Agri-food Industry—A Review," Food Bioprocess Technol. 2:P115-121, (2009).

N. Kiga et al., "CNT-FET Gas Sensor Using a Functionalized Ionic Liquid as Gate," The University of Tokyo, 978-1-4673-0324-8/12, 796-799 (2012).

K. Ishizu et al. "Carbon Dioxide Detection by Surface Plasmon Resonance with Ionic Liquid," The University of Tokyo, 978-1-4673-0324-8/12, 784-787 (2012).

A. Star et al. "Nanoelectronic Carbon Dioxide Sensors," Adv. Mater. 16, No. 22, 2049-2052, (2004).

International Search Report issued in PCT/JP2012/083879, dated Apr. 2, 2013.

Office Action dated Aug. 20, 2015 issued for corresponding Chinese Patent Application No. 2012 800 60964.4.

Oter et al., "Room temperature ionic liquids as optical sensor matrix materials for gaseous and dissolved $CO_2$", Sensors and Actuators B 117 (2006) 295-301, dated Dec. 28, 2005.

Yun-liang Fu, "Surface plasmon resonance gas sensor with composite of Ag/$TiO_2$ film layer", Sensor and Micro-System, vol. 27, No. 12, dated Jun. 14, 2008.

The extended European search report dated Jul. 15, 2015 issued for corresponding European Patent Application No. 12 86 4780.7.

Star et al.: "Nanoelectronic CO2 Breath Sensors", 2005 NSTI Nanotechnology Conference and Trade Show—NSTI Nanotech 2005 Technical Proceedings, vol. 1, pp. 104-107, dated May 12, 2005.

Ong et al.: "A Carbon Nanotube-based Sensor for CO2 Monitoring", Sensors, Molecular Diversity Preservation International (MDPI), vol. 2001, No. 1(6), pp. 193-205, dated Nov. 2, 2001.

Heller et al.: "Influence of Electrolyte Composition on Liquid-Gated Carbon Nanotube and Graphene Transistors", Journal of the American Chemical Society, vol. 132, No. 48, pp. 17149-17156, dated Dec. 8, 2010.

Kiga et al.: "CNT-FET Gas Sensor Using a Functionalized Ionic Liquid as Gate", Micro Electro Mechanical Systems (MEMS), 2012 IEEE 25th International Conference, MEMS 2012 Paris France, pp. 796-799, dated Jan. 29, 2012.

The extended European search report dated Nov. 26, 2015 issued for corresponding European Patent Application No. 12865116.3.

Nylander et al.: "Gas Detection by Means of Surface Plasmon Resonance", Sensors and Actuators, 3 (1982) (1), pp. 79-88.

* cited by examiner

| | h1 [μm] | h2 [μm] | IONIC LIQUID AMOUNT |
|---|---|---|---|
| DEVICE A | 50 | 300 | 21 [μl] |
| DEVICE B | 250 | 35 | 12 [μl] |

FIG. 24

|  | D [μm] | IONIC LIQUID AMOUNT | RESPONSE TIME [min] | | |
| --- | --- | --- | --- | --- | --- |
|  |  |  | 10% | 25% | 50% |
| DEVICE A | 350 | 21 [μl] | 21 | 20 | 33 |
| DEVICE B | 285 | 12 [μl] | 7 | 12 | 13 |

DECREASE BY 56% ON AVARAGE

GAS SENSOR

CROSS REFERENCE TO RELATED APPLICATIONS

This application is a U.S. National Stage application under 35 U.S.C. §371 of International Patent Application Serial No. PCT/JP2012/083880, filed Dec. 27, 2012, which Application claims the benefit of priority of Japanese Patent Application No. JP2012-004964, filed Jan. 13, 2012, the disclosures of each of which are expressly incorporated by reference in their entireties. This application is related to co-pending application U.S. application Ser. No. 14/366,912 entered into U.S. on Jun. 19, 2014 under 35 U.S.C. §371 of International Patent Application Serial No. PCT/JP2012/083879, filed Dec. 27, 2012, which Application claims the benefit of priority of Japanese Patent Application No. JP2012-004963, filed Jan. 13, 2012, the disclosures of each of which are expressly incorporated by reference in their entireties.

TECHNICAL FIELD

The present invention relates to a gas sensor, and is suitable to be applied to detection of, for example, gases such as $CO_2$ and $NH_3$.

BACKGROUND ART

In recent years, studies on gas sensors that detect $CO_2$, for example, have been made at the requests for environmental monitoring. As a gas sensor of this kind, an infrared light absorption type gas sensor (NDIR: Nondispersive infrared detector) is known (for example, refer to Non Patent Literature 1). Further, as another gas sensor, a gas sensor using surface plasmon resonance (SPR) is known (for example, refer to Non Patent Literature 2).

CITATION LIST

Non Patent Literature

Non Patent Literature 1: S. Neethirajan, D. S. Jayas, and S. Sadistap, "Carbon dioxide ($CO_2$) sensors for the agri-food industry—a review," Food Bioprocess Technol., vol. 2, pp. 115-121, 2009.
Non Patent Literature 2: Shozo Miwa, and Tsuyoshi Arakawa, "Selective gas detection by means of surface plasmon resonance sensors," Thin Solid Films, vol. 281, pp. 466-468, 1996.

SUMMARY OF INVENTION

Technical Problem

However, in the infrared light absorption type gas sensor shown in the former, a light absorption path needs to be provided, and therefore, there arises the problem that the optical system is increased in size. Further, in the gas sensor in the latter does not require a light absorption path, and the size can be reduced correspondingly, but since the refractive index to be measured is substantially proportional to a molecular weight. Accordingly, it is difficult to measure, for example, the gas with a small molecular weight such as $CO_2$. Therefore, realization of the gas sensor including a novel configuration that is also capable of detecting a gas with a small molecular weight has been desired.

Consequently, the present invention is made in consideration of the above respect, and has an object to propose a gas sensor capable of performing detection of a gas with a novel configuration while achieving reduction in size.

Solution to Problem

The present invention is a gas sensor that detects a gas that is a target of detection, the gas sensor including: a prism having a metal layer in an irradiation range of an incident light incident from a light source, and changing a path of the incident light at the metal layer to emit the incident light as an exit light; and a gas absorbing liquid provided on a surface of the metal layer, and capable of absorbing the gas, and is featured in that a dielectric constant of the gas absorbing liquid changes due to absorption of the gas in the gas absorbing liquid, and based on a change in light intensity of the exit light by a surface plasmon resonance phenomenon that occurs in the metal layer in response to the change in the dielectric constant, the gas is detected.

Advantageous Effect of Invention

According to the present invention, the light absorption path as in the prior art is not needed, and therefore, reduction in size can be achieved correspondingly. Also, a gas is absorbed in the gas absorbing liquid, and a dielectric constant of the gas absorbing liquid that changes by absorbing the gas can be measured according to the change in the light intensity that occurs by a surface plasmon resonance phenomenon in the metal layer. Thus, the gas sensor including a novel configuration that can detect the gas based on the change in the light intensity can be realized.

BRIEF DESCRIPTION OF DRAWINGS

FIG. 24 is a table showing experimental results of gas sensors using the device A and the device B respectively.

REFERENCE SIGNS LIST 1, 51 Gas sensor
3 Frame body (holding means)
6 Prism
7 Metal layer
IL Ionic liquid (gas adsorbing liquid)
53 Coating film (holding means)

DESCRIPTION OF EMBODIMENTS

Hereinafter, embodiments of the present invention will be described in detail based on the drawings.

(1) Outline of Gas Sensor of the Present Invention

Figure 1:
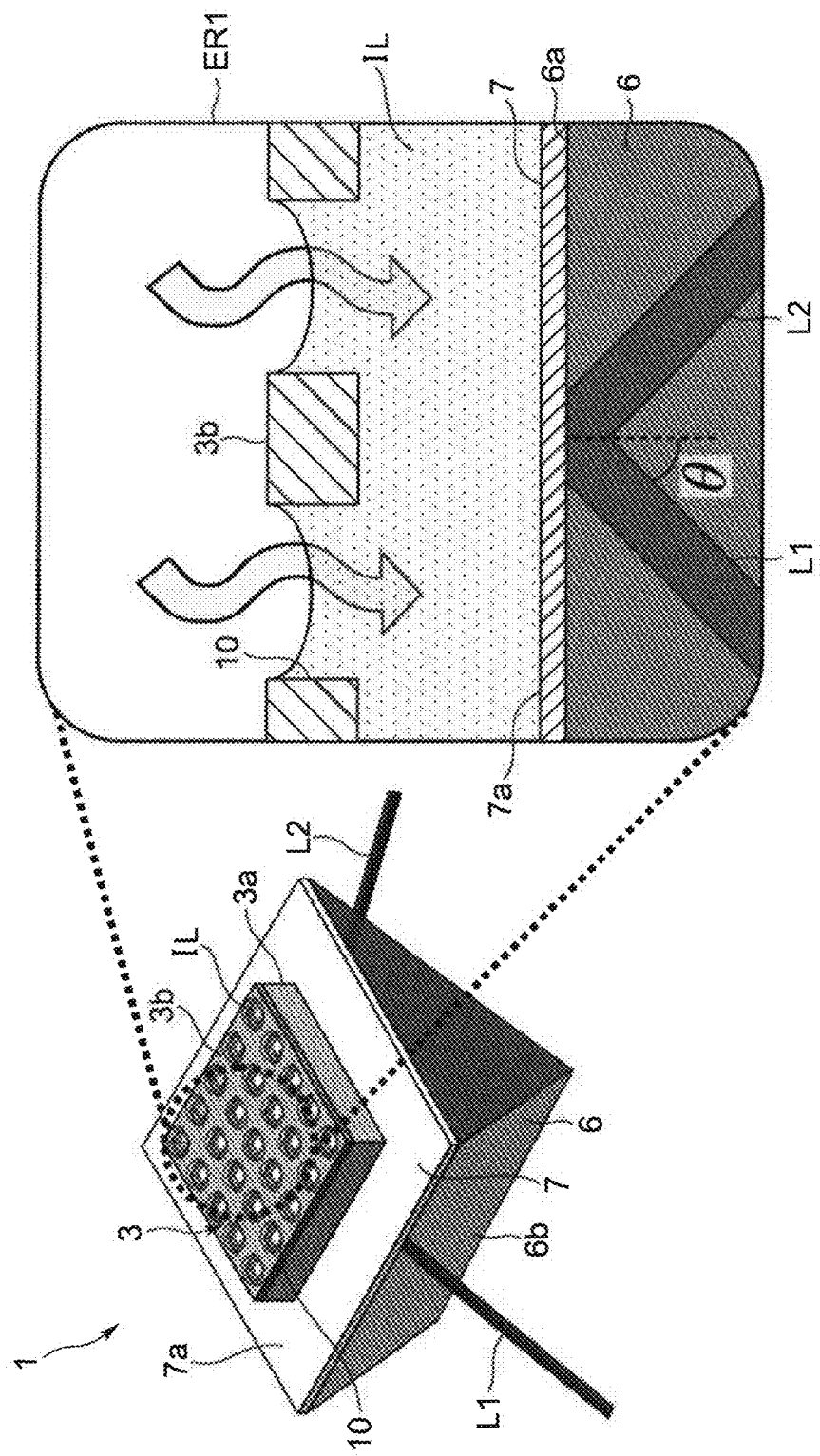
FIG. 1 is a schematic view showing a configuration of a gas sensor according to the present invention.

In FIG. 1, a gas sensor according to the present invention is denoted by 1, and the gas sensor 1 is configured to be able to detect, for example, $CO_2$, as a target of detection. In practice, the gas sensor 1 has a configuration having a prism 6 on which an incident light L1 from a light source not illustrated is incident, including a metal layer 7 in an irradiation range of the incident light L1 that is incident on the prism 6, and provided with an ionic liquid IL on a surface 7a of the metal layer 7.

In practice, the prism 6 is formed from, for example, a transparent material such as glass and acryl, and allows the incident light L1 emitted from the light source to pass through an inside thereof. Further, in the case of the embodiment, the prism 6 is formed into a substantially triangular prism shape, so that the incident light L1 can be incident on a quadrangular incidence plane 6b. The prism 6 is configured such that the incident light L1 incident from the incidence plane 6b passes through the inside thereof and can reach the metal layer 7 that is deposited on another quadrangular irradiation plane 6a, and can exit as an exit light L2 from another quadrangular exit plane after the path of the incident light L1 is changed at the metal layer 7.

Further, in the metal layer 7, a frame body 3 configured by a wall portion 3a and a top plate portion 3b is fixedly attached to a surface 7a, and the ionic liquid IL is kept on the surface 7a by the frame body 3. In practice, the frame body 3 is formed from silicon, for example, and a height thereof is set at 250 [μm]. Further, in the frame body 3, the plate-shaped top plate portion 3b is provided at a frame-shaped wall portion 3a of one side set at 10 [mm], an internal space surrounded by the surface 7a of the metal layer 7, the wall portion 3a, and the top plate portion 3b is formed, so that the ionic liquid IL is kept in the internal space.

Here, the frame body 3 has a configuration in which a plurality of through-holes 10 are provided by being bored in the top plate portion 3b, and as shown in an area ER1 in which a part of the gas sensor 1 of FIG. 1 is enlarged, the ionic liquid IL in the internal space is exposed to an outside from the through-holes 10, so that the ionic liquid IL in the internal space can contact outside air around an outside of the frame body 3. Thereby, the ionic liquid IL held in the frame body 3 can absorb a gas that is a target of detection contained in the outside air. Incidentally, in the frame body 3, the through-holes 10 bored in the top plate portion 3b are microscopic, and therefore, the ionic liquid IL keeps staying in the frame body 3 by the surface tension without leaking out from the through-holes 10 and can be held stably on the surface 7a of the metal layer 7, though the ionic liquid IL injected into the internal space is exposed to outside air by the through-holes 10.

Here, the metal layer 7 on which the ionic liquid IL is placed is formed from an Au or Cr/Au material, for example, and has a film thickness set at approximately 50 nm. When the metal layer 7 is irradiated with the incident light L1 passing through the inside of the prism 6 at an incidence angle θ, the metal layer 7 can change the path by reflecting the incident light L1. Note that here, the incidence angle θ refers to an angle of the incident light L1 with respect to a perpendicular line orthogonal to the plane of the metal layer 7. In addition to the above configuration, the metal layer 7 is configured to be able to generate a surface plasmon resonance phenomenon in accordance with a state of a dielectric constant of the ionic liquid IL placed on the surface 7a, when the incident light L1 is emitted.

Incidentally, a surface plasmon resonance phenomenon refers to a phenomenon in which when the incident light L1 is caused to be incident on the prism 6, evanescent waves that are always generated in the prism surface on which the metal layer 7 is deposited, and surface plasmon waves that are excited in the surface 7a of the metal layer 7 resonate, and light intensity (hereinafter, also called reflection intensity) of the exit light L2 that reflects at the metal layer 7 decreases.

Here, the ionic liquid IL as a gas absorbing liquid is formed from, for example, [EMIM][BF$_4$] (1-ethyl-3-methylimidazolium tetrafluoroborate), [BMIM][BF$_4$] (1-butyl-3-methylimidazolium tetrafluoroborate), [BMIM][PF$_6$] (1-butyl-3-methylimidazolium hexafluorophosphate), or [OMIM][Br] (1-n-octyl-3-methylimidazolium bromide), and other than the above, [Hmpy][Tf$_2$N], [HMIM][Tf$_2$N], [BMIM][Tf$_2$N], [C$_6$H$_4$F$_9$min][Tf$_2$N], [AMIM][BF$_4$], [Pabim][Bf$_4$], [Am-im][DCA], [Am-im][BF$_4$], [BMIM][BF$_4$]+PVDF, [C$_3$NH$_2$mim][CF$_6$SO$_3$]+PTFE, [C$_3$NH$_2$mim][Tf$_2$N]+PTFE, [H$_2$NC$_3$H$_6$mim][Tf$_2$N]+cross-linked Nylon66, P[VBBI][BF$_4$], P[MABI][BF$_4$], P[VBBI][Tf$_2$N], P[VBTMA][BF$_4$], P[MATMA][BF$_4$] or the like, and in accordance with the kind of a gas to be a target of detection, the ionic liquid that can absorb the gas can be properly selected.

Here, when the gas sensor 1 that can detect $CO_2$, for example, is made, [EMIM][BF$_4$], [BMIM][BF$_4$], [BMIM][PF$_6$], [Hmpy][Tf$_2$N], [HMIM][Tf$_2$N], [BMIM][Tf$_2$N], [C$_6$H$_4$F$_9$mim][Tf$_2$N], [AMIM][BF$_4$], [Pabim][BF$_4$], [Am-im][DCA], [Am-im][BF$_4$], [BMIM][BF$_4$]+PVDF,

[C$_3$NH$_2$mim][CF$_6$SO$_3$]+PTFE, [C$_3$NH$_2$mim][Tf$_2$N]+PTFE, [H$_2$NC$_3$H$_6$mim][Tf$_2$N]+cross-linked Nylon66, P[VBBI][BF$_4$], P[MABI][BF$_4$], P[VBBI][Tf$_2$N], P[VBTMA][BF$_4$], P[MATMA][BF$_4$] or the like that can absorb CO$_2$ is used as the ionic liquid IL. Further, when the gas sensor 1 that can detect NH$_3$ is made, ionic liquids that absorb water in general, such as [EMIM][BF$_4$] capable of absorbing NH$_3$ are used as the ionic liquid IL. Note that to the ionic liquid IL, for example, PEI (polyethyleneimine) may be added.

Further, in the aforementioned embodiment, the case in which the ionic liquid IL is applied as the gas absorbing liquid is described, but the present invention is not limited to this, and, for example, various other gas absorbing liquids such as hydroxide aqueous solutions of an alkali metal and an alkaline earth metal may be applied. Note that when hydroxide aqueous solutions of an alkali metal and an alkaline earth metal are used as the gas absorbing liquids, the gas absorbing liquids can absorb CO$_2$, and therefore, the gas sensor the detection target of which is CO$_2$ can be realized.

The ionic liquid IL like this is configured such that when the ionic liquid IL absorbs the gas that is a target of detection, the dielectric constant thereof can change in accordance with an absorption amount of the gas. The metal layer 7 on which the ionic liquid IL is placed is configured such that when the dielectric constant changes in the ionic liquid IL, the light intensity (reflection intensity) of the exit light L2 can change in accordance with the change in the dielectric constant.

Figure 2A:
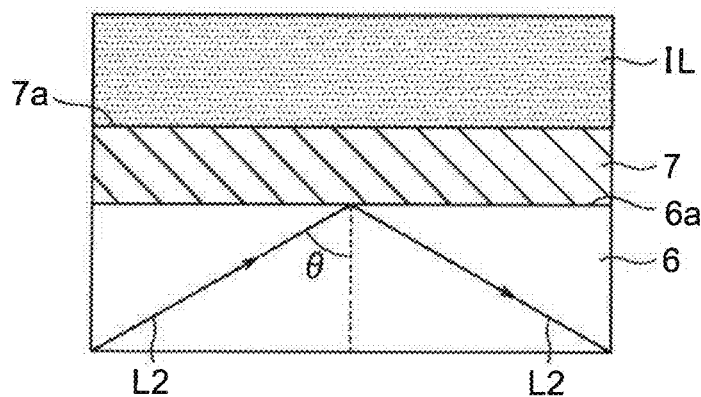
FIG. 2 is a schematic view presented for explanation of a surface plasmon resonance phenomenon.
Figure 2B:
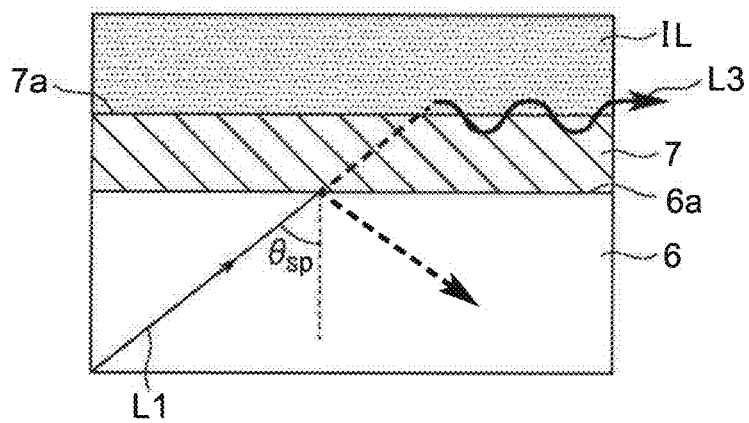

In practice, as shown in FIG. 2A, when the gas that is a target of detection is not contained in outside air, for example, change in the dielectric constant by the gas does not occur in the ionic liquid IL, and the metal layer 7 can reflect the incident light L1 emitted at the incidence angle θ and can allow the incident light L1 to exit with a predetermined light intensity as the exit light L2. Meanwhile, as shown in FIG. 2B, when the gas that is a target of detection is contained in outside air, for example, the dielectric constant of the ionic liquid IL changes due to the gas, and even when the incident light L1 is caused to be incident on the metal layer 7 at the same incidence angle θ, the surface plasmon wave L3 that is generated in a plane direction of the metal layer 7 by receiving the influence of the change of the dielectric constant resonates with an evanescent wave, and can decrease the light intensity (reflection intensity) of the exit light L2.

Figure 3:
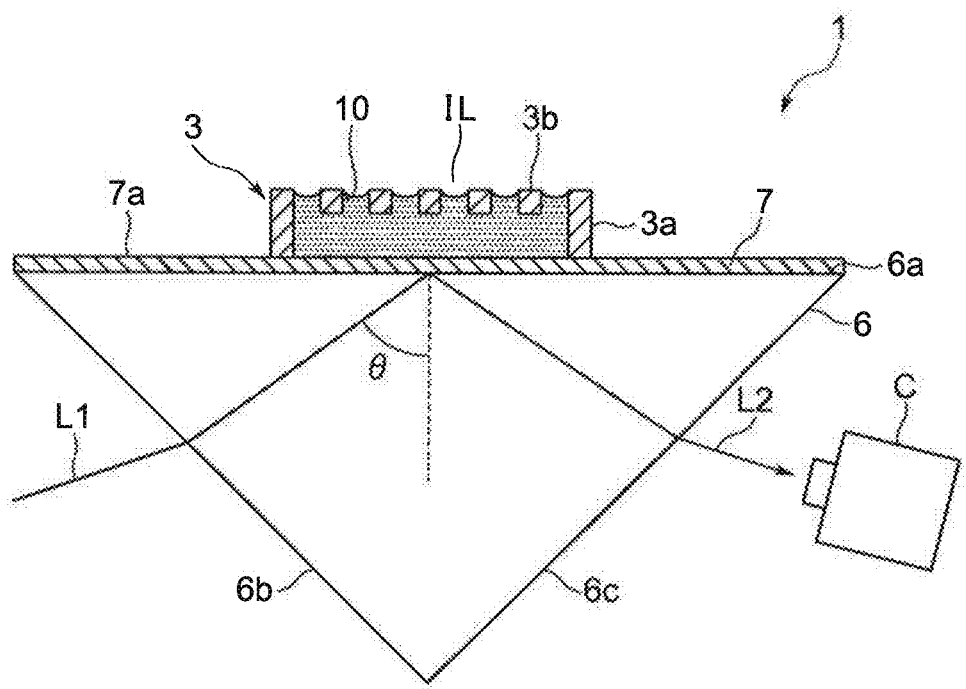
FIG. 3 is a sectional view showing a sectional side configuration of the gas sensor according to the present invention.

As shown in FIG. 3, the gas sensor includes an intensimeter C that measures the light intensity of the exit light L2 at a position facing an exit plane 6c, and can measure a change in the light intensity of the exit light L2 that occurs due to a surface plasmon resonance phenomenon by the intensimeter C. The gas sensor 1 is configured to measure the change in the light intensity of the exit light L2 by the surface plasmon resonance phenomenon that occurs on the metal layer 7 in accordance with the change in the dielectric constant of the ionic liquid IL by the intensimeter C, and to be able to detect the gas contained in the outside air based on the measurement result thereof.

Figure 4:
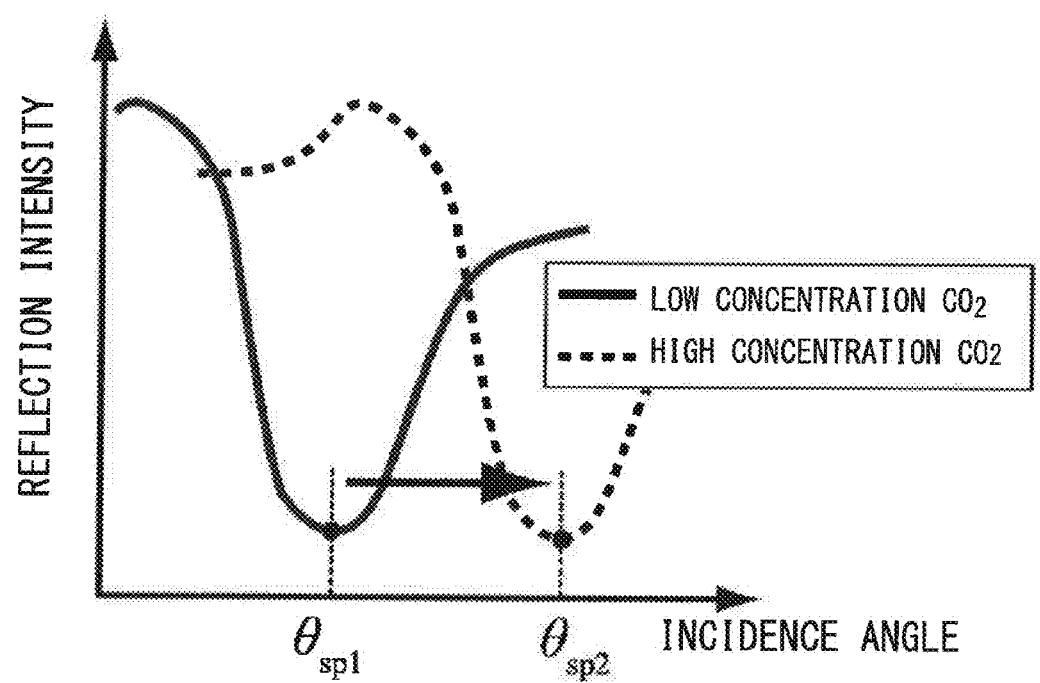
FIG. 4 is a graph showing a relation of an incidence angle and a reflection intensity.

In practice, as shown in FIG. 4, when the concentration of CO$_2$ that is a target of detection is low, the measurement result that the reflection intensity decreases due to a surface plasmon resonance phenomenon at an incidence angle $θ_{sp1}$, for example, is obtained in this gas sensor 1. In contrast with this, when the concentration of CO$_2$ that is the target of detection is high, the measurement result that the reflection intensity decreases by a surface plasmon resonance phenomenon at an incidence angle $θ_{sp2}$ that differs from the incidence angle $θ_{sp1}$ is obtained in the gas sensor 1, a dip angle at which the reflection intensity decreases by a surface plasmon resonance phenomenon can change from the incidence angle $θ_{sp1}$ to the incidence angle $θ_{sp2}$ in accordance with the concentration of CO$_2$. Thus, in this gas sensor 1, it can be detected whether or not CO$_2$ is contained in outside air by a predetermined concentration or more, based on the change in the light intensity of the exit light L2 by the surface plasmon resonance phenomenon that occurs in the metal layer 7 in accordance with the change in the dielectric constant of the ionic liquid IL. Further, the dip angle at which the reflection intensity decreases by a surface plasmon resonance phenomenon changes in accordance with the concentration of CO$_2$. From this, in this gas sensor 1, the concentration of CO$_2$ contained in outside air can be estimated based on the change amount of the light intensity of the exit light L2 and the change amount of the dip angle.

(2) Method of Producing Gas Sensor

Figure 5:
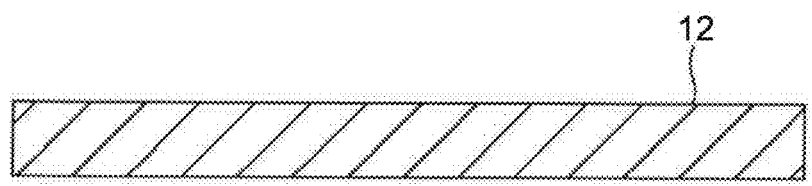
FIG. 5 is a schematic view presented for explanation (1) of a method of producing a frame body.
Figure 6:
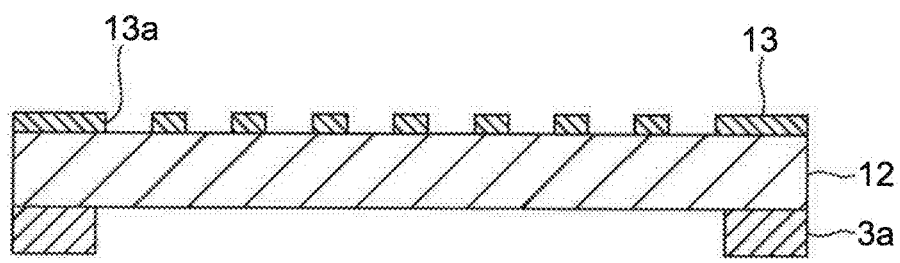
FIG. 6 is a schematic view presented for explanation (2) of the method of producing the frame body.

Next, a method of producing the gas sensor 1 of the present invention will be described. Here, a method of producing the frame body is described, and then, the method of producing the gas sensor using the frame body will be described in sequence. First of all, as shown in FIG. 5, a silicon substrate 12 of a thickness of 250 [μm] to be the top plate portion 3b is prepared, and as shown in FIG. 6, a resist layer 13 having through-holes 13a of each 500 [μm] in length and width at intervals of 650 [μm] is formed on one surface of the silicon substrate 12. Further, apart from this, the wall portion 3a is formed on the other surface of the silicon substrate 12 from a resist material (KMPR-1035 made by Nippon Kayaku Co., Ltd.) of a thickness of 30 [μm], for example, by spin coating and patterning.

Figure 7:
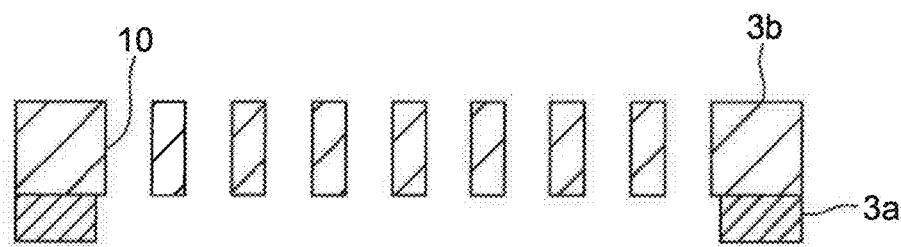
FIG. 7 is a schematic view presented for explanation (3) of the method of producing the frame body.
Figure 8:
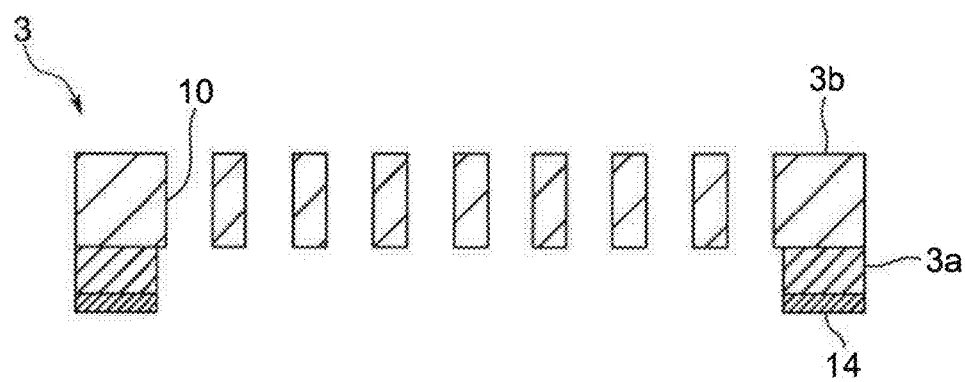
FIG. 8 is a schematic view presented for explanation (4) of the method of producing the frame body.

Next, the silicon substrate 12 is etched with use of the resist layer 13 provided on the one surface of the silicon substrate 12, and then, the resist layer 13 is removed, and the top plate portion 3b having the plurality of through-holes 10 is formed as shown in FIG. 7. Hence, the frame body 3 to which the frame-shaped wall portion 3a is fixedly attached to the other surface along the frame of the top plate portion 3b in a mesh shape is formed. Next, as shown in FIG. 8, an adhesive layer 14 formed from polydimethylsiloxane (PDMS), for example, is formed on a bottom surface portion of the wall portion 3a to fixedly attach the frame body 3 to the metal layer 7 on the prism 6 that will be described later.

Figure 9:
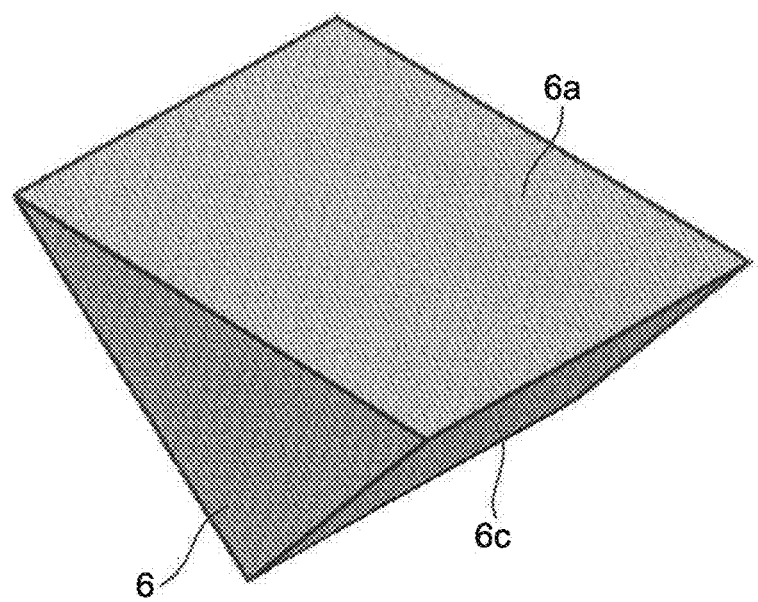
FIG. 9 is a schematic view presented for explanation (1) of a method of producing the gas sensor.
Figure 10:
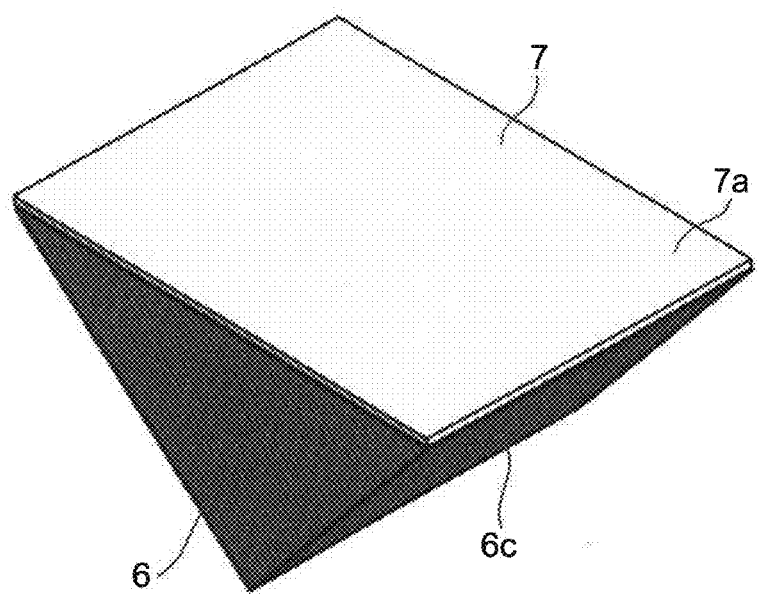
FIG. 10 is a schematic view presented for explanation (2) of the method of producing the gas sensor.

Next, the method of producing the gas sensor 1 using the frame body 3 produced as above will be described. Here, the prism 6 formed from glass in a triangular prism shape (for example, made from SF11 glass, with a refractive index of 1.774 with a light wavelength of 675 [nm]) as shown in FIG. 9 is prepared first of all, and thereafter, the metal layer 7 formed from CR/Au (2 [nm]/50 [nm]) as shown in FIG. 10 is deposited on only the irradiation plane 6a flat and formed into a quadrangular shape. Note that the film thickness of the metal layer 7 is optimized to maximize the sensitivity for surface plasmon resonance.

Figure 11:
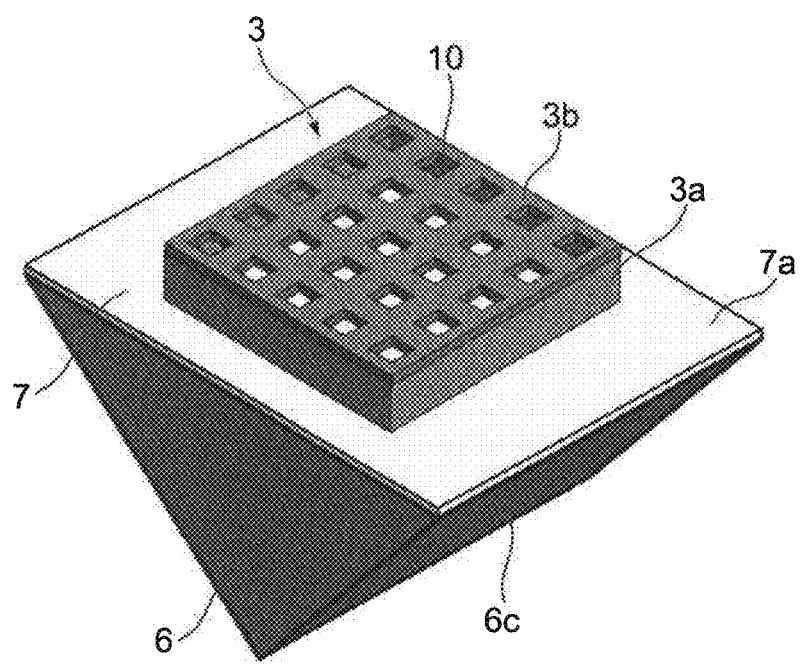
FIG. 11 is a schematic view presented for explanation (3) of the method of producing the gas sensor.
Figure 12:
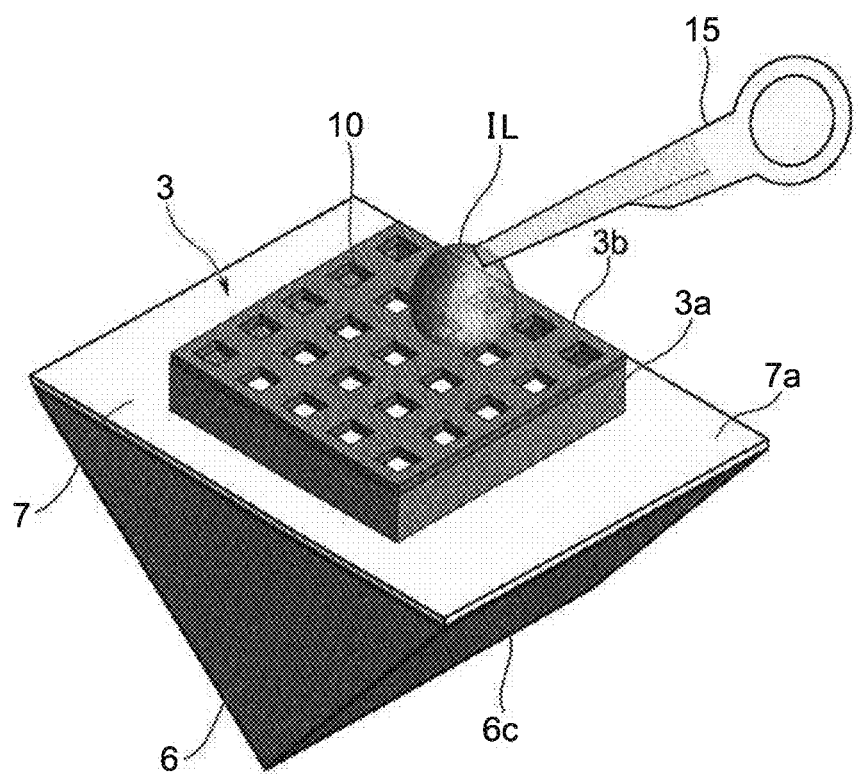
FIG. 12 is a schematic view presented for explanation (4) of the method of producing the gas sensor.
Figure 13:
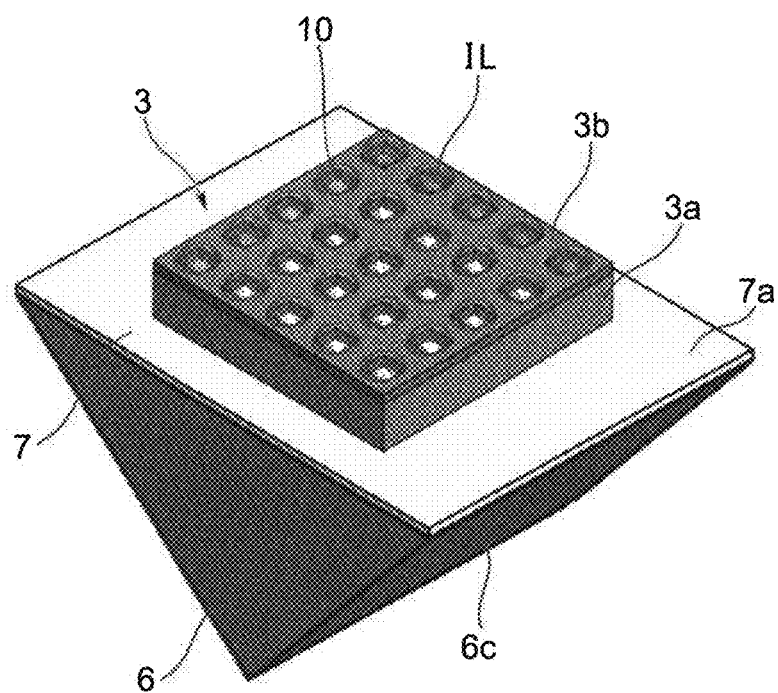
FIG. 13 is a schematic view presented for explanation (5) of the method of producing the gas sensor.

Next, as shown in FIG. 11, the wall portion 3a of the frame body 3 produced in advance is placed on the metal layer 7 on the prism 6, and then heated by a heater at 110[° C.] for five minutes to allow the wall portion 3a of the frame body 3 to be fixedly attached to the metal layer 7 by the adhesive layer 14. Next, as shown in FIG. 12, the ionic liquid IL is injected into the internal space of the frame body 3 from the through-holes 10 of the frame body 3 via injection means 15 such as a dropping pipette, and thereby the gas sensor 1 of the present invention as shown in FIG. 13 can be produced.

(3) Verification Test

Figure 14:
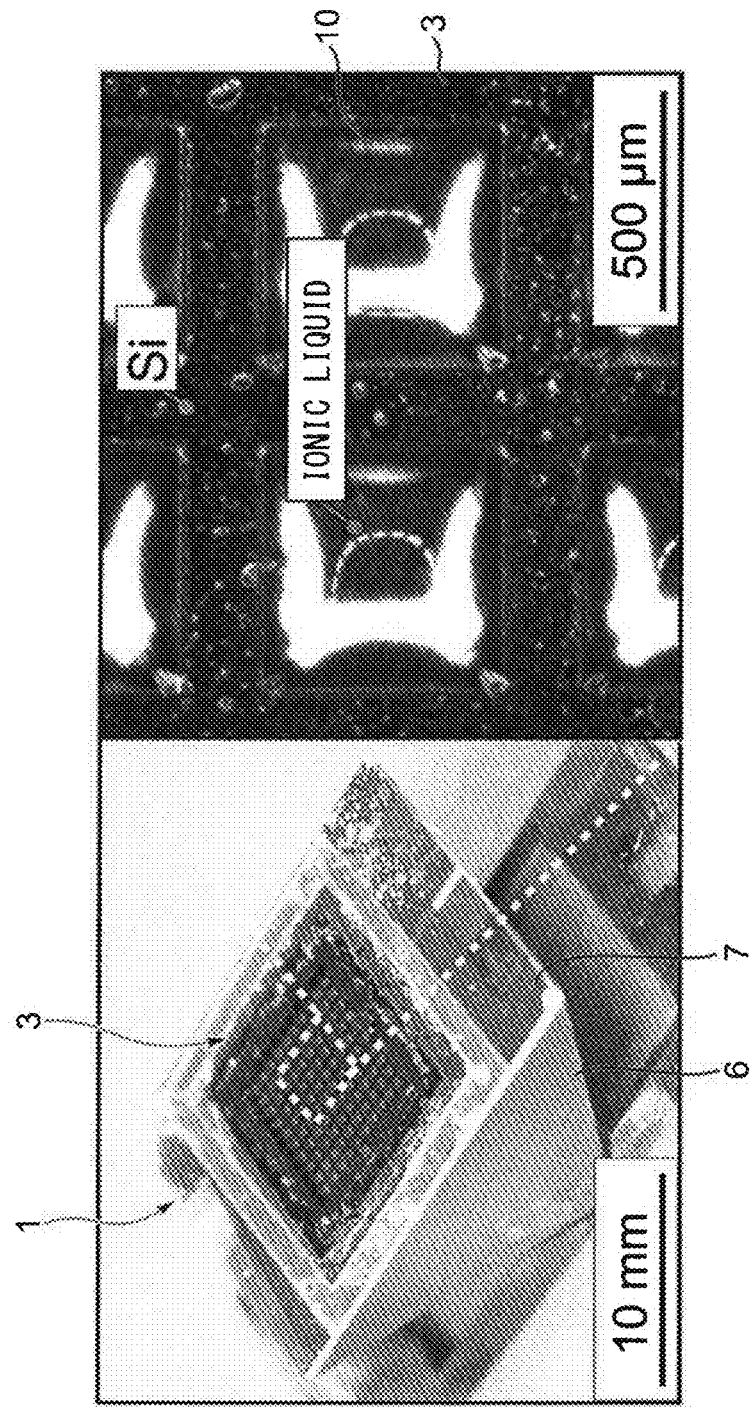
FIG. 14 is a photograph showing a configuration of a gas sensor that was actually produced.

Next, various verification tests will be described. Here, in accordance with the production method described above, as shown in FIG. 14, the gas sensor 1 was produced, in which the metal layer 7 was kept substantially horizontal, and the ionic liquid IL was exposed to an outside from the through-holes 10 of 500 [μm]×500 [μm] of the frame body 3 while 10 [μl] of the ionic liquid IL was held in the frame body 3 of 10 [mm]×10 [mm]. Note that an opening ratio to the outside of the frame body 3 in the gas sensor 1 was set at 60[%].

Figure 15:
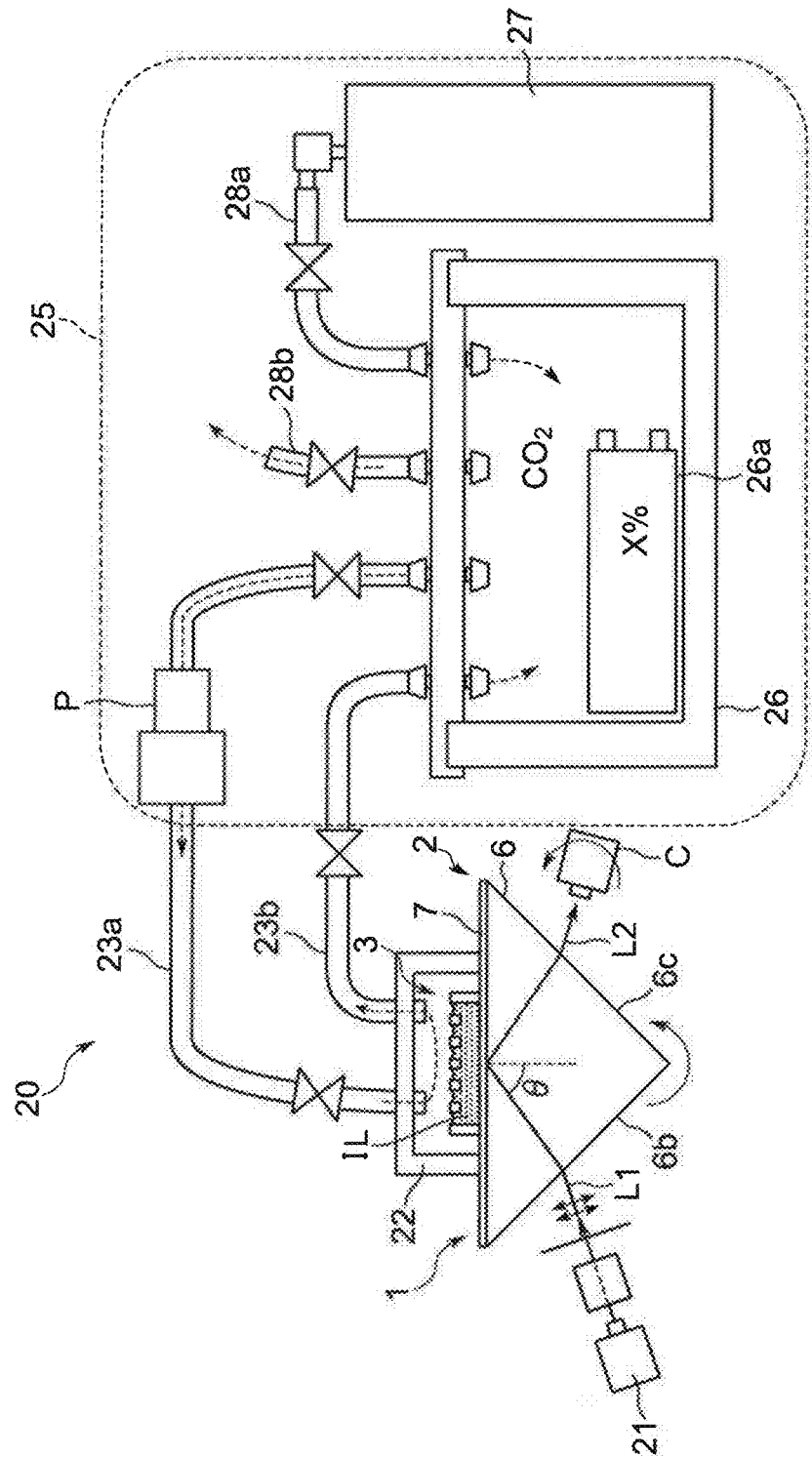
FIG. 15 is a schematic view showing an entire configuration of an experimental apparatus.

Subsequently, with use of an experimental apparatus 20 as shown in FIG. 15, verification was conducted on whether or not $CO_2$ that is a target of detection can be detected in the gas sensor 1. In practice, the experimental apparatus 20 includes a gas supply device 25, and a gas which was adjusted to have a predetermined $CO_2$ concentration was supplied to an isolation chamber 22 provided in the gas sensor 1 from the gas supply device 25. Here, the gas supply device 25 includes a chamber 26, a gas storage section 27 and a pump P, $CO_2$ was supplied into the chamber 26 from the gas storage section 27, and a gas adjusted to have a predetermined $CO_2$ concentration was generated in the chamber 26 with a detected concentration of a concentration sensor 26a in the chamber 26 as a measure.

Further, the gas supply device 25 recovered the gas to the chamber 26 from the isolation chamber 22 via a recovery tube 23b while supplying the gas in the chamber 26 to the isolation chamber 22 via a supply tube 23a from the chamber 26 by a pump P, so as to circulate the gas. Note that the chamber 26 was provided with an exhaust tube 28b, and the gas in the chamber 26 was discharged to the outside from the exhaust tube 28b in accordance with necessity. The isolation chamber 22 was formed by a housing and was installed on the metal layer 7 in such a manner as to cover the entire frame body 3 on the metal layer 7 in the gas sensor 1 to isolate the ionic liquid IL of the gas sensor 1 from the outside air. Thereby, in this experiment, the ionic liquid IL of the gas sensor 1 was disposed in the gas of a predetermined $CO_2$ concentration generated in the chamber 26.

Further, in this experimental apparatus 20, a light source 21 that emits a TM polarized wave of a wavelength of 675 [nm] was provided, and the TM polarized wave was emitted onto the incidence plane 6b of the prism 6 as the incident light L1. In practice, the laser light from a laser diode was polarized by a polarizing plate, the incident light L1 that was made a spot of 0.3 [nm] by a slit was generated by the light source 21, and emitted to the prism 6. Further, here, the incident light L1 was emitted toward the metal layer 7 from the incidence plane 6b of the prism 6 of the gas sensor 1 and the path of the incident light L1 was changed at the metal layer 7 of the gas sensor 1, and thereby being emitted from the exit plane 6c as the exit light L2. Further, the intensimeter C was disposed at a position facing the exit plane 6c, and the light intensity of the exit light L2 was measured by the intensimeter C.

With use of the experimental apparatus 20 as above, a gas (namely, a gas that does not contain $CO_2$) with the concentration of $CO_2$ of 0×10⁵ [ppm] was filled in the isolation chamber 22 first of all, the incident light L1 is emitted to the prism 6 from the light source 21 after stabilization, after which, the incidence angle θ of the incident light L1 was changed from 50[°] to 60[°] with angle resolution of 0.05[°], and the light intensity (reflection intensity) of the exit light L2 at this time was measured by the intensimeter C. Further, after the isolation chamber 22 was refreshed, a gas with the concentration of $CO_2$ of 5.0×10⁵ [ppm] was filled in the isolation chamber 22, the incident light L1 is emitted to the prism 6 from the light source 21 after stabilization, after which, the incidence angle θ of the incident light L1 was changed from 50[°] to 60[°] with angle resolution of 0.05[°], and the light intensity (reflection intensity) of the exit light L2 at this time was measured by the intensimeter C.

Figure 16:
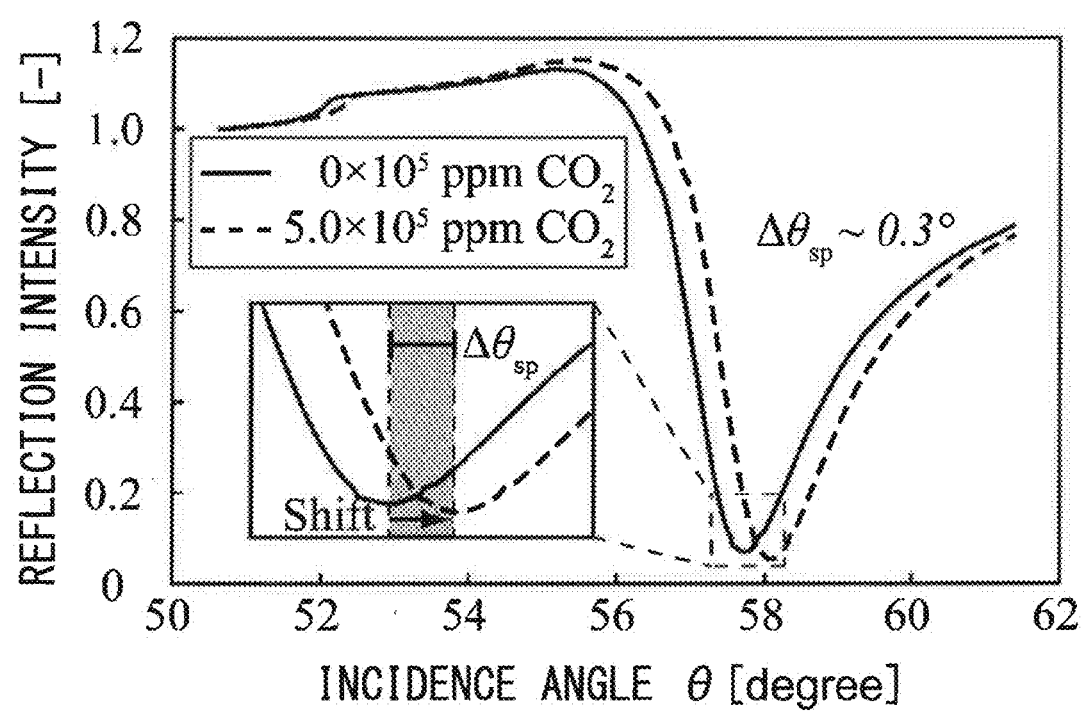
FIG. 16 is a graph showing relations of incidence angles and reflection intensity in the case of a mixture gas of $CO_2$ and outside air, and in the case of only outside air.
Figure 17:
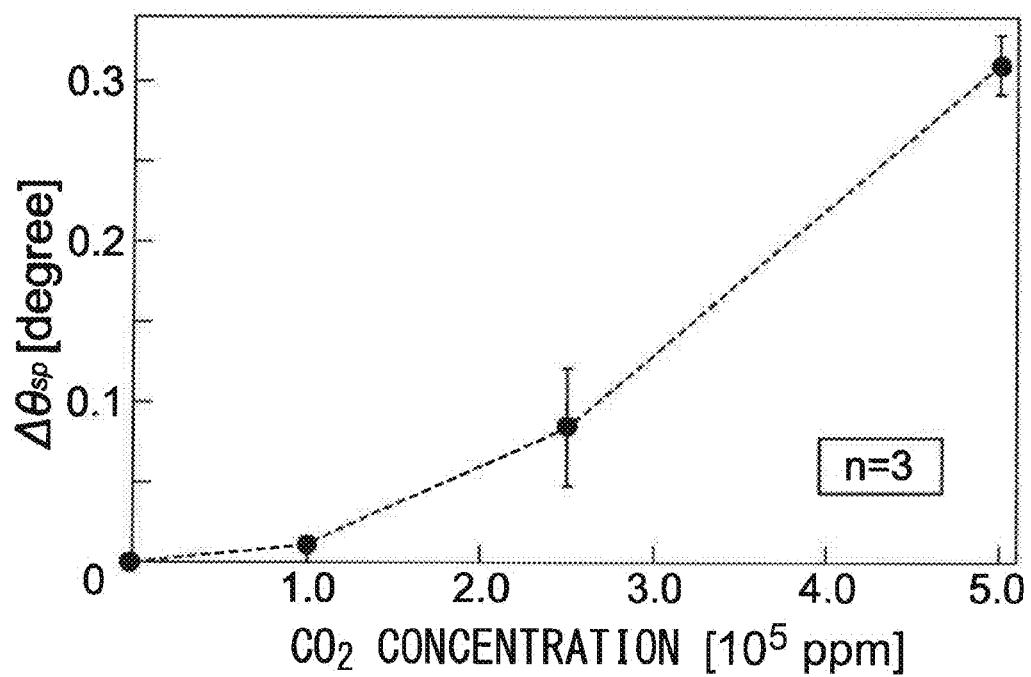
FIG. 17 is a graph showing a relation of a dip angle shift and a $CO_2$ concentration.

Consequently, a result as shown in FIG. 16 was obtained. From FIG. 16, when attention is paid to the dip angle at which the lowest reflection intensity appears, when the $CO_2$ concentration in the gas becomes high, a dip angle shift $\Delta\theta_{sp}$ representing a shift amount of the dip angle becomes 0.3[°], and it has been able to be confirmed that the dip angle shifts. Next, when the dip angle shifts $\Delta\theta_{sp}$ at the time of making the $CO_2$ concentration 1.0×10⁵ [ppm], 2.5×10⁵ [ppm] and 5.0×10⁵ [ppm] were examined, a result as shown in FIG. 17 was obtained. From FIG. 17, it was confirmed that in this gas sensor 1, as the $CO_2$ concentration becomes higher, the dip angle shift $\Delta\theta_{sp}$ also becomes larger, and therefore, it was confirmed that by measuring the value of the dip angle shift $\Delta\theta_{sp}$, the $CO_2$ concentration in the outside air also can be estimated.

Figure 18:
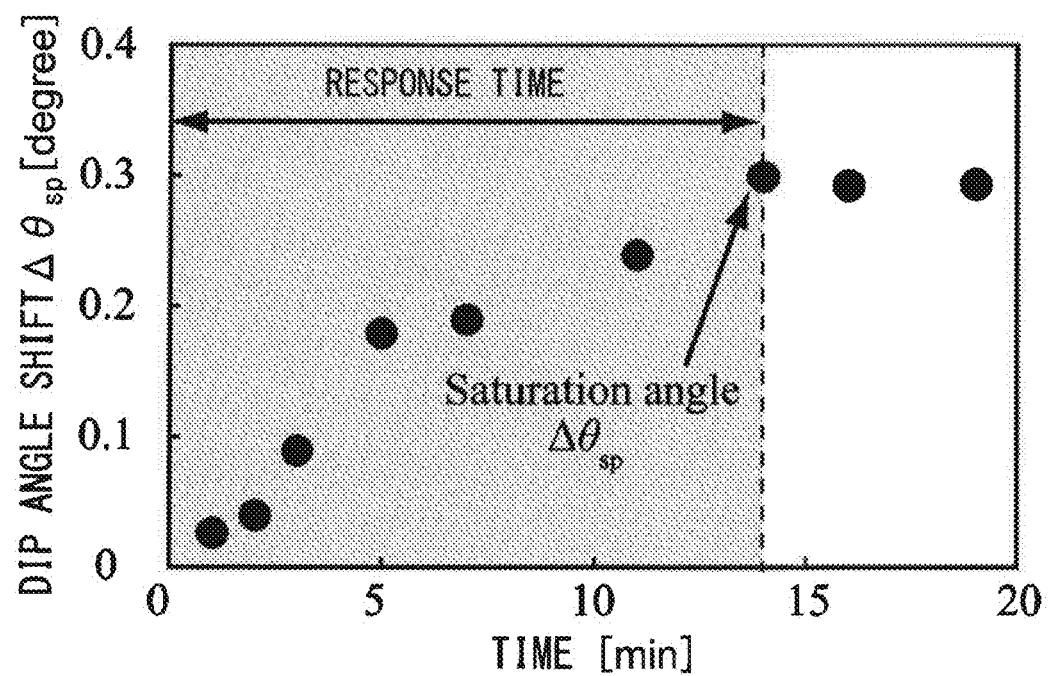
FIG. 18 is a graph showing a change with time of the dip angle shift.

Next, when a response time until the dip angle shift $\Delta\theta_{sp}$ changed after the $CO_2$ concentration was changed was examined, a result as shown in FIG. 18 was obtained. From FIG. 18, it was found out that when the $CO_2$ gas of 5.0×10⁵ [ppm] is supplied into the isolation chamber 22, the dip angle shift $\Delta\theta_{sp}$ is stabilized after 13 minutes of the supply of the $CO_2$ gas, it was further found out that with the $CO_2$ gas of 1.0×10⁵ [ppm] and the $CO_2$ gas of 2.5×10⁵ [ppm], average response times are respectively 7 minutes and 12 minutes, and it was confirmed that gas detection can be performed by minutes.

Figure 19:
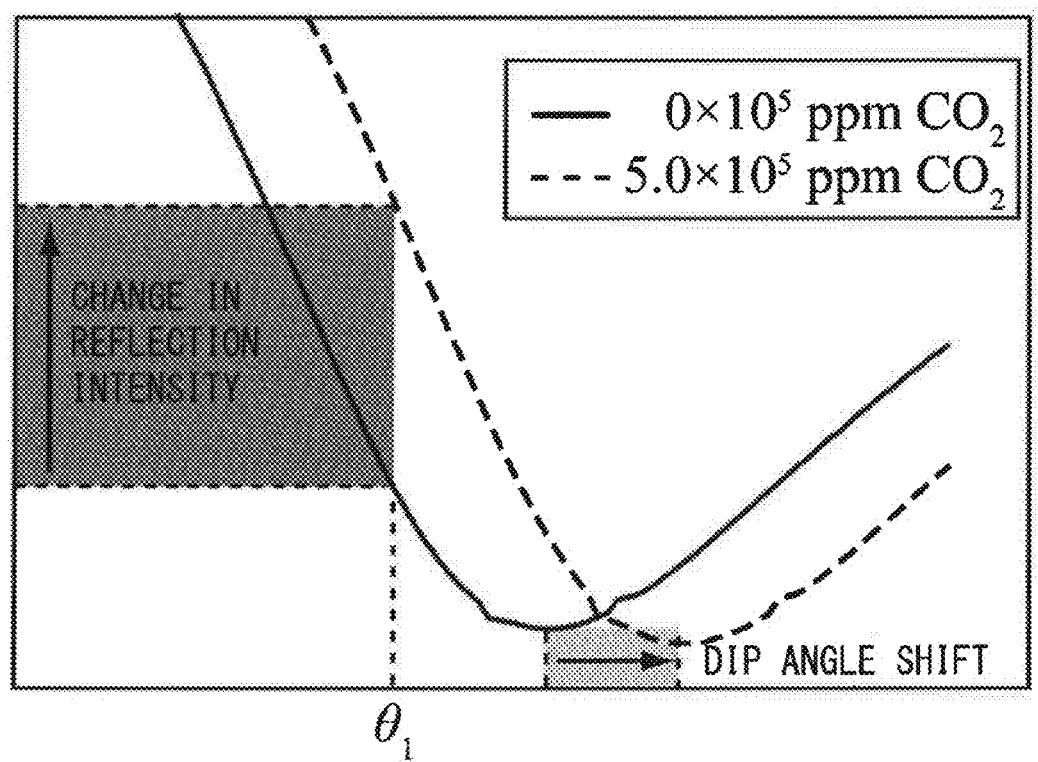
FIG. 19 is a graph showing relations of the dip angle shifts and changes in reflection intensity in the case of a mixture gas of $CO_2$ and outside air, and in the case of only outside air.

Here, FIG. 19 is a graph comparing the dip angle shift $\Delta\theta_{sp}$ obtained in the gas sensor 1 when the $CO_2$ concentrations were made 0×10⁵ [ppm] and 5.0×10⁵ [ppm], and a ratio of change in reflection intensity. In FIG. 19, as a region in which the change in the reflection intensity is examined, attention was paid to the incidence angle $\theta_1$ at which the light intensity of the exit light L2 starts to reduce by a surface plasmon resonance phenomenon. As shown in FIG. 19, as the measurement result obtained from the gas sensor 1, it was found out that the ratio of the change in the reflection intensity at the incidence angle $\theta_1$ is larger as compared with the dip angle shift $\Delta\theta_{sp}$. From this, it was found out that in the gas sensor 1, the change amount of the reflection intensity which has a larger change amount as compared with the dip angle shift $\Delta\theta_{sp}$ is measured, and the gas in the outside air is detected based on the change amount of the reflection intensity, whereby even if a very small amount of gas is contained in the outside air, the gas can be easily detected with a larger change amount than the dip angle shift $\Delta\theta_{sp}$.

Figure 20:
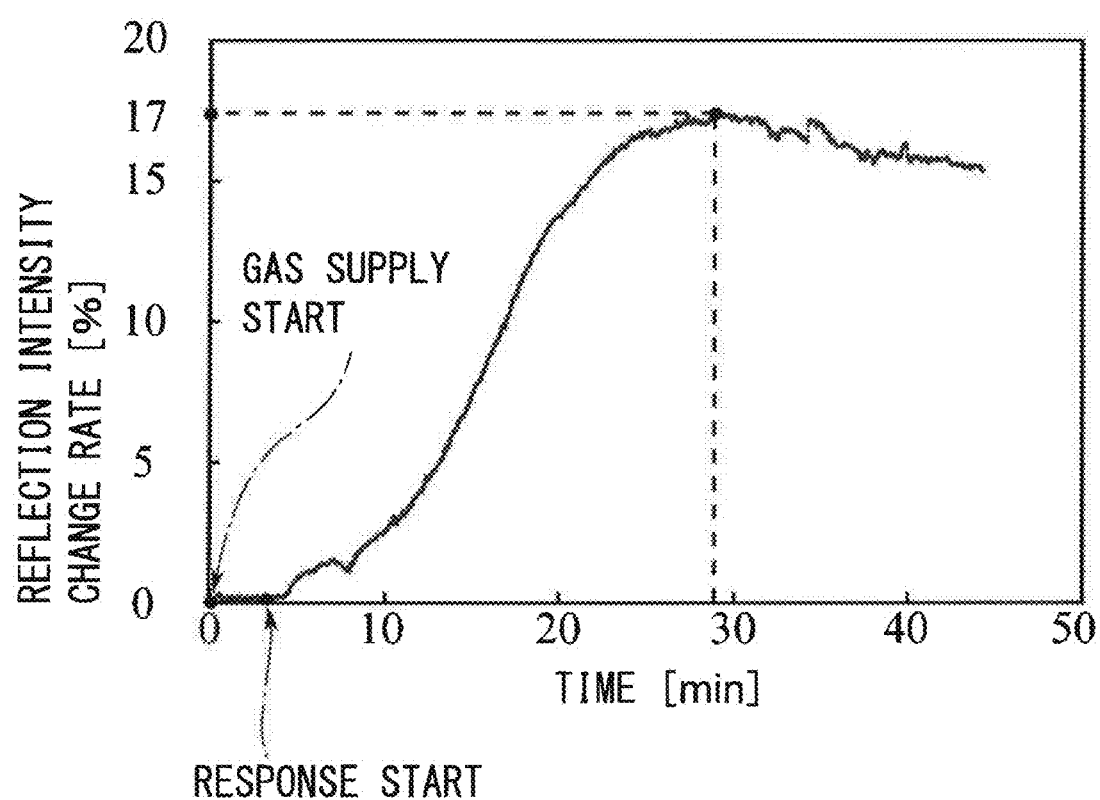
FIG. 20 is a graph showing a change with time of a reflection intensity change rate.

Further, FIG. 20 shows a result of examining a change with time of a reflection intensity change rate from a time of starting to supply a gas with a $CO_2$ concentration of 6500 [ppm] to the isolation chamber 22. The reflection intensity change rate started to increase after a lapse of four minutes from the start of supply of the gas, and had a stable value after 28 minutes. Further, the reflection intensity change rate increased by 17[%] (from 10 [μW] to 11.7 [μW]). Furthermore, from FIG. 20, when the reflection intensity change rate was less than 2[%] (0.2 [μW]), an unstable behavior was shown, in which the reflection intensity change rate is temporarily reduced or the like. Accordingly, it was found out that in the gas sensor 1, detecting the $CO_2$ concentration by using the reflection intensity change rate of 2[%] or more in which the reflection intensity change rate stably increases in proportion to the $CO_2$ concentration is also preferable as one example thereof. In this case, the $CO_2$ concentration is stably detectable up to the $CO_2$ concentration of approximately 700 [ppm] (calculated from the experimental value of the reflection intensity change rate 17[%] with the $CO_2$ concentration of 6500 [ppm]).

Figure 21:
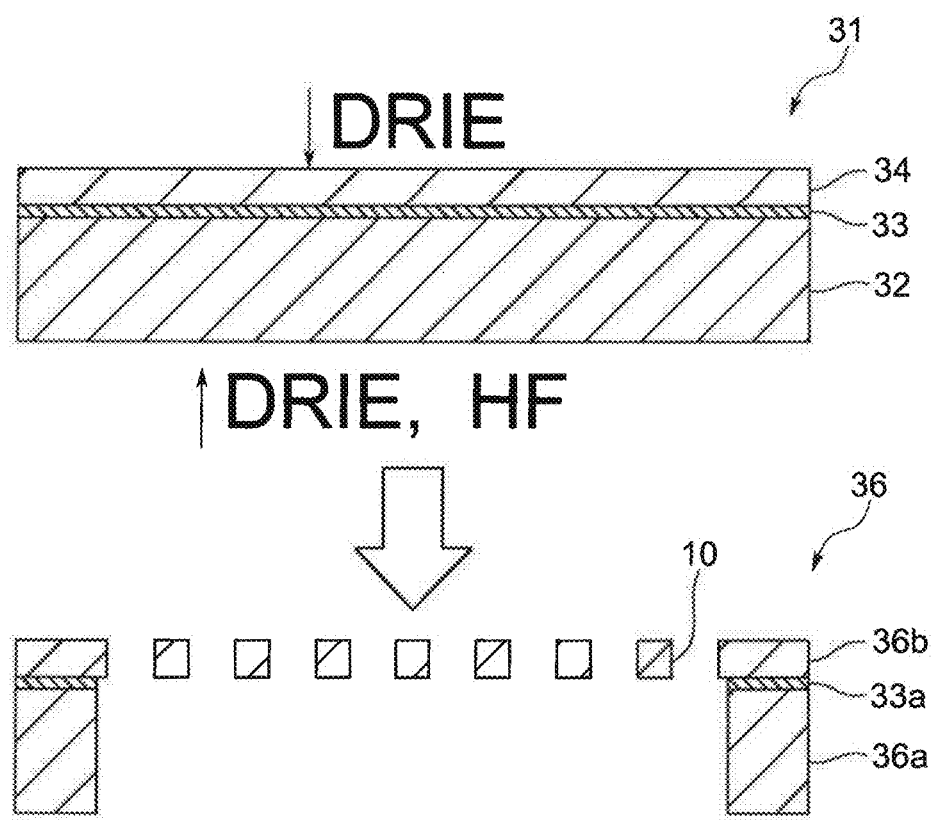
FIG. 21 is a schematic view showing a method of producing a device A.

Next, two kinds of frame bodies that have different sizes of the internal spaces were prepared, and in two kinds of gas sensors provided with the frame bodies, reaction times (response times) in which the reflection intensity change rates changed when the $CO_2$ concentration was changed were examined. In practice, as shown in FIG. 21, first of all, an SOI wafer 31 in which an upper silicon layer 34 was provided on a lower silicon layer 32 via a silicon oxide film 33 was prepared. Next, the lower silicon layer 32 and the upper silicon layer 34 were processed by DRIE (Deep Reactive Ion Etching) that is a micropore forming technique, and then were conducted a cleaning by hydrogen fluoride (HF). After the cleaning, a wall portion 36a in a frame shape was formed from the lower silicon layer 32, a top plate portion 36b in a mesh shape having a plurality of through-holes 10 was formed from the upper silicon layer 34, and a first frame body 36 in which the top plate portion 36b was stacked on the wall portion 36a via the silicon oxide film 33a was produced, and was set as a device A.

Figure 22:
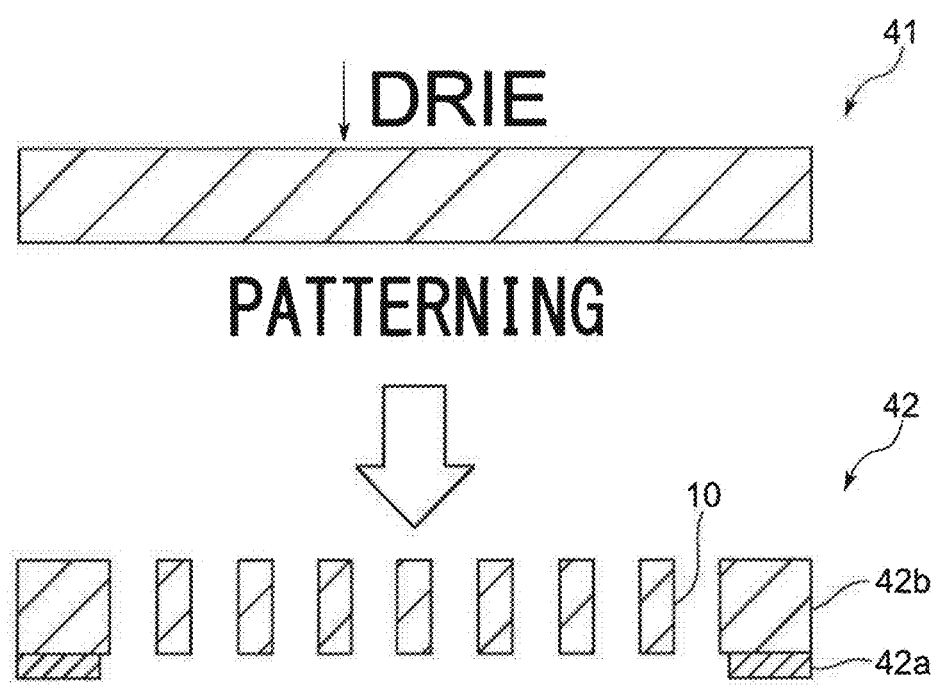
FIG. 22 is a schematic view showing a method of producing a device B.

Further, apart from the above, as shown in FIG. 22, a substrate 41 formed from a photosensitive resin (KMPR-1035) was prepared. The substrate 41 was patterned by DRIE (Deep Reactive Ion Etching) that is a micropore forming technique, and a top plate portion 42b in a mesh shape having a plurality of through-holes 10 was produced. Further, a frame-shaped wall portion 42a was formed along a frame of the top plate portion 42b, and a second frame body 42 was produced and was set as a device B.

Figure 23:
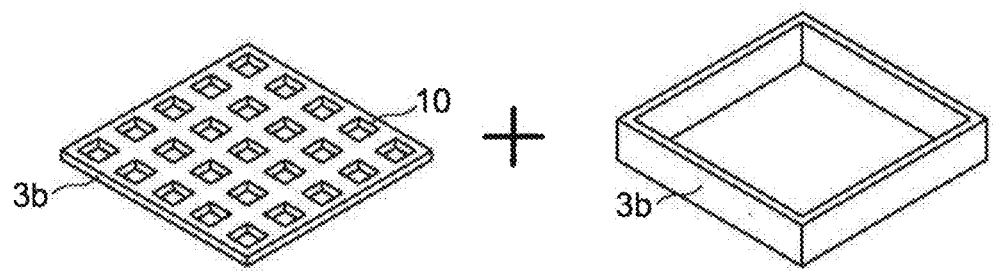
FIG. 23 is a table showing respective dimensions of the device A and the device B.

As shown in FIG. 23, for example, with a height of the top plate portion 3b being set as h1, and a height of the wall portion 3a being set as h2, the heights h1 and h2 were respectively measured similarly with respect to the device A and the device B. As a result, as in a table shown in FIG. 23, in the device A, the height h1 of the top plate portion 36b was 50 [μm], the height h2 of the wall portion 36a was 300 [μm], and a liquid amount of the ionic liquid IL that was able to be injected into the internal space when the device A was fixedly attached onto the metal layer 7 of the gas sensor 1 was 21 [μl]. Meanwhile, with respect to the device B, the height h1 of the top plate portion 42b was 250 [μm], the height h2 of the wall portion 42a was 35 [μm], and a liquid amount of the ionic liquid IL that was able to be injected into the internal space when the device B was fixedly attached onto the metal layer 7 of the gas sensor 1 was 12 [μl].

Subsequently, by using of the experimental apparatus 20, with respect to the gas sensors provided with the device A and the device B respectively as above, when the gases the $CO_2$ concentrations of which were 10[%], 25[%] and 50[%] were respectively supplied to the isolation chambers 22, and the response times until the dip angles were generated after start of gas supply were examined, a result as shown in FIG. 24 was obtained. Note that in FIG. 24, a total height of the heights h1 and h2 is described as D [μm]. From the result of FIG. 24, it was confirmed that in the gas sensor provided with the device B with a smaller liquid amount of the ionic liquid IL, the response time is shorter by 56[%] on average, and the response time becomes expedited. Accordingly, it was confirmed that when a gas sensor is produced, in which a response time is short with respect to the gas that is a target of detection, the liquid amount of the ionic liquid IL can be made small.

(4) Operation and Effect

In the above configuration, the gas sensor 1 has the prism 6 including the metal layer 7 in the irradiation range of the incident light L1 that is caused to be incident from the light source, and changes the path of the incident light L1 at the metal layer 7 of the prism 6 to emit the incident light L1 as the exit light L2. Further, in the gas sensor 1, the ionic liquid IL that can absorb the gas that is a target of detection is provided on the surface 7a of the metal layer 7, and the dielectric constant of the ionic liquid IL changes as a result of the ionic liquid IL absorbing the gas, and the light intensity of the exit light L2 changes by a surface plasmon resonance phenomenon that occurs in the metal layer 7 in accordance with the change of the dielectric constant. Thereby, in the gas sensor 1, the change in the light intensity of the exit light L2 is measured, and the gas in outside air can be detected based on the tendency of the change in the light intensity of the exit light L2.

Further, in the gas sensor 1, the light absorption path as in the prior art is not needed, and therefore, the size can be reduced correspondingly. Furthermore, in the gas sensor 1, even the gas with a small molecular weight such as $CO_2$ can be absorbed by the ionic liquid IL, and the dielectric constant of the ionic liquid IL that changes by absorbing the gas can be measured from the change in the reflection intensity that occurs by a surface plasmon resonance phenomenon in the metal layer 7. Therefore, the gas sensor 1 can detect even the gases with small molecular weights, which are conventionally difficult to measure.

Furthermore, in the gas sensor 1 of the present invention, by only changing the kind of the ionic liquid IL provided on the metal layer 7, not only a gas with a small molecular weight but also gases with various molecular weights can be easily detected. Like this, in the present invention, the change in the dielectric constant of the ionic liquid IL can be measured according to the change in the light intensity that occurs by a surface plasmon resonance phenomenon in the metal layer 7, and therefore, the gas sensor 1 that is made of novel configuration that can detect a gas based on the change in the light intensity can be realized.

Further, in the gas sensor 1, a gas is detected based on the change amount of a dip angle that occurs by a surface plasmon resonance phenomenon in the metal layer 7, whereby a gas in outside air can be easily detected with the dip angle which has the smallest reflection intensity and easily recognizable as the measure. Furthermore, in the gas sensor 1, the frame body 3 that holds the ionic liquid IL on the metal layer 7 is provided, whereby even when an external force is applied to the metal layer 7, the ionic liquid IL can be kept to be held on the metal layer 7 stably.

(5) Other Embodiments

Note that the present invention is not limited to the present embodiment, and can be carried out by being variously modified within the range of the gist of the present invention. In the embodiment described above, as the holding means, the case of applying the frame body 3 in which a plurality of through-holes 10 are provided by being bored in the top plate portion 3b and causes the metal layer 7 to hold the ionic liquid IL by surrounding the ionic liquid IL with the top plate portion 3b and the wall portion 3a is described, but the present invention is not limited to this. A coating film that is formed from a material that allows a gas to pass through such as parylene, and causes the metal layer 7 to hold the ionic liquid IL by covering the entire surface of the semispherical ionic liquid IL that is dropped on the metal layer 7 may be applied.

Figure 25:
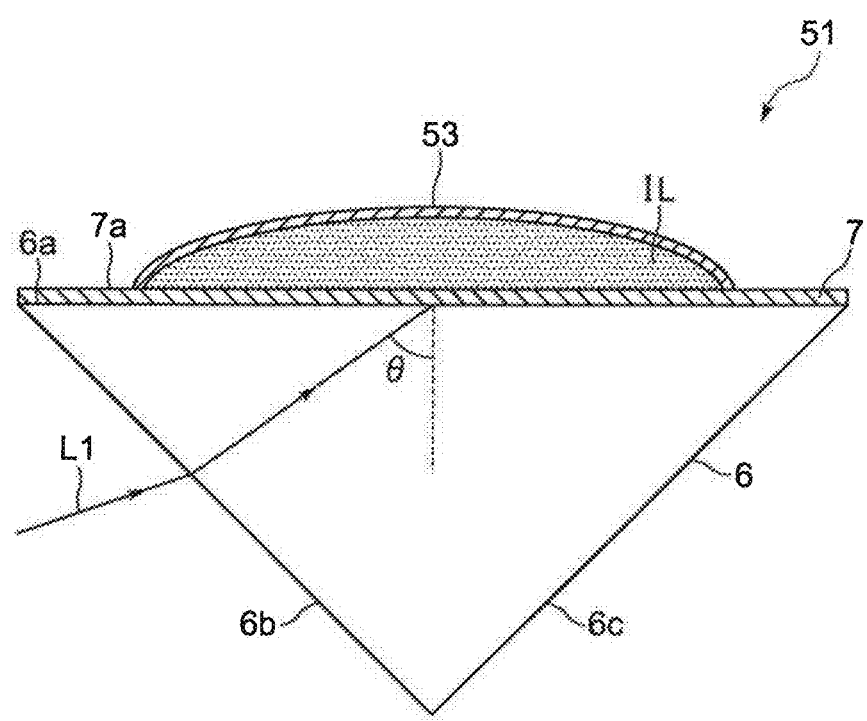
FIG. 25 is a sectional view showing a sectional side configuration of a gas sensor according to another embodiment.

In practice, as in FIG. 25 showing a gas sensor by assigning the components corresponding to those in FIG. 3 with the same reference signs, a gas sensor 51 has a configuration in which a coating film 53 formed from, such as parylene that allows outside air to pass through, is formed on the metal layer 7, and the ionic liquid IL is stored in the coating film 53. In this case, in the gas sensor 51, even if an external force is applied to the metal layer 7 and the metal layer 7 is tilted or the like, the ionic liquid IL can be kept to be held on the metal layer 7 stably by the coating film 53 as the holding means. Incidentally, the gas sensor 51 can be produced by forming the coating film 53 on the metal layer 7 in advance from a coating material that allows outside air to pass through such as parylene, injecting the ionic liquid IL into the coating film 53 and sealing the ionic liquid IL.

Furthermore, as another embodiment, a configuration may be adopted, in which the metal layer 7 of the prism 6 is installed as a bottom surface in a box-shaped storage section in which the ionic liquid IL is stored, and the incident light L1 is emitted from the light source disposed diagonally above. Such gas sensors with the disposition relations of the prism 6 provided with the metal layers 7 and the ionic liquid IL properly changed may be applied in accordance with service conditions.

The invention claimed is:

1. A gas sensor that detects a gas that is a target of detection, comprising:

a prism having a metal layer in an irradiation range of an incident light incident from a light source, and changing a path of the incident light at the metal layer to emit the incident light as an exit light;

a gas absorbing liquid provided on a surface of the metal layer, and capable of absorbing the gas; and holding means covering the gas absorbing liquid, and causing the gas absorbing liquid to be held on the metal layer, wherein a dielectric constant of the gas absorbing liquid changes due to absorption of the gas in the gas absorbing liquid, and based on a change in light intensity of the exit light by a surface plasmon resonance phenomenon that occurs in the metal layer in response to the change in the dielectric constant, the gas is detected, and the holding means includes an internal space surrounded and formed by the surface of the metal layer, a wall portion, and a top plate portion having a plurality of through-holes bored therein, said wall portion being fixedly attached to the metal layer, so that the gas absorbing liquid is kept in the internal space while being exposed to an outside from the through-holes.

2. The gas sensor according to claim 1, wherein the gas is detected based on a change amount of a dip angle that occurs by the surface plasmon resonance phenomenon when the gas absorbing liquid absorbs the gas.

3. The gas sensor according to claim 1, wherein the gas is detected based on a change amount of reflection intensity that occurs by the surface plasmon resonance phenomenon when the gas absorbing liquid absorbs the gas.

4. The gas sensor according to claim 1, wherein the gas absorbing liquid in the internal space keeps staying in the holding means due to surface tension without leaking out from the through-holes.

5. The gas sensor according to claim 1, wherein the gas absorbing liquid is an ionic liquid.

6. The gas sensor according to claim 1, wherein the gas absorbing liquid is a hydroxide aqueous solution of an alkali metal and an alkaline earth metal.

7. The gas sensor according to claim 1, wherein the top plate portion and the wall portion are made of silicon.

8. The gas sensor according to claim 1, wherein the gas is $CO_2$ gas.

9. The gas sensor according to claim 8, wherein the gas absorbing liquid comprises an ionic liquid selected from the group consisting of [EMIM][$BF_4$], [BMIM][$BF_4$], [BMIM][$PF_6$], [Hmpy][$Tf_2N$], [HMIM][$Tf_2N$], [BMIM][$Tf_2N$], [$C_6H_4F_9$mim][$Tf_2N$], [AMIM][$BF_4$], [Pabim][$BF_4$], [Am-im][DCA], [Am-im][$BF_4$], [BMIM][$BF_4$]+PVDF, [$C_3NH_2$mim][$CF_6SO_3$]+PTFE, [$C_3NH_2$mim][$Tf_2N$]+PTFE, [$H_2NC_3H_6$mim][$Tf_2N$]+cross-linked Nylon66, P[VBBI][$BF_4$], P[MABI][$BF_4$], P[VBBI][$Tf_2N$], P[VBTMA][$BF_4$], and P[MATMA][$BF_4$].

10. The gas sensor according to claim 9, wherein the gas absorbing liquid further comprises polyethyleneimine.

* * * * *